(12) United States Patent
Minagawa

(10) Patent No.: US 10,251,980 B2
(45) Date of Patent: Apr. 9, 2019

(54) SURFACE-MODIFIED METAL AND METHOD FOR MODIFYING METAL SURFACE

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 23 days.

(21) Appl. No.: 14/954,019

(22) Filed: Nov. 30, 2015

(65) Prior Publication Data

US 2016/0184487 A1 Jun. 30, 2016

(30) Foreign Application Priority Data

Dec. 26, 2014 (JP) ................. 2014-264608

(51) Int. Cl.
| | | |
|---|---|---|
| *C08K 9/06* | (2006.01) | |
| *A61L 31/04* | (2006.01) | |
| *C08L 33/04* | (2006.01) | |
| *A61L 29/02* | (2006.01) | |
| *A61L 29/08* | (2006.01) | |
| *A61L 29/14* | (2006.01) | |
| *A61L 31/02* | (2006.01) | |
| *A61L 31/10* | (2006.01) | |
| *A61L 31/14* | (2006.01) | |
| *C08F 292/00* | (2006.01) | |
| *C08K 5/5425* | (2006.01) | |

(52) U.S. Cl.
CPC ............ *A61L 31/048* (2013.01); *A61L 29/02* (2013.01); *A61L 29/085* (2013.01); *A61L 29/145* (2013.01); *A61L 31/022* (2013.01); *A61L 31/10* (2013.01); *A61L 31/14* (2013.01); *A61L 31/145* (2013.01); *C08F 292/00* (2013.01); *C08K 5/5425* (2013.01); *A61L 2400/10* (2013.01); *A61L 2420/02* (2013.01); *A61L 2420/06* (2013.01); *A61L 2420/08* (2013.01)

(58) Field of Classification Search
USPC ............................ 523/105, 203; 427/2.1, 2.3
See application file for complete search history.

(56) References Cited

U.S. PATENT DOCUMENTS

| | | | |
|---|---|---|---|
| 3,532,655 A * | 10/1970 | Radlove ............... | C09D 125/14 525/155 |
| 5,218,070 A | 6/1993 | Blackwell | |
| 5,693,034 A | 12/1997 | Buscemi et al. | |
| 6,001,894 A | 12/1999 | Ottersbach et al. | |
| 6,013,855 A * | 1/2000 | McPherson ............. | A61L 27/34 427/2.24 |
| 6,221,425 B1 | 4/2001 | Michal et al. | |
| 6,391,463 B1 * | 5/2002 | Fan ......................... | C07F 7/0818 428/447 |
| 9,695,331 B2 * | 7/2017 | Horgan ................. | C09D 133/14 |
| 2003/0215649 A1 | 11/2003 | Jelle | |
| 2006/0013853 A1 * | 1/2006 | Richard .................. | A61L 31/10 424/423 |
| 2009/0171302 A1 | 7/2009 | Eramo, Jr. et al. | |
| 2009/0176183 A1 * | 7/2009 | Conrad .................... | A61C 7/20 433/20 |
| 2010/0145286 A1 * | 6/2010 | Zhang .................... | A61L 17/005 604/265 |
| 2011/0059874 A1 | 3/2011 | Rooijmans et al. | |
| 2012/0059111 A1 | 3/2012 | Sandhu et al. | |
| 2013/0242467 A1 * | 9/2013 | Biler ..................... | C09D 5/4476 361/504 |
| 2013/0266815 A1 * | 10/2013 | Horgan ................. | C09D 133/14 428/447 |
| 2016/0008520 A1 | 1/2016 | Minagawa et al. | |
| 2016/0159019 A1 * | 6/2016 | Bruce .............. | B29D 11/00038 351/159.33 |
| 2017/0056563 A1 | 3/2017 | Minagawa | |

FOREIGN PATENT DOCUMENTS

| | | | |
|---|---|---|---|
| CN | 101970583 A | | 2/2011 |
| CN | 103209717 A | | 7/2013 |
| EP | 0872512 | * | 10/1998 |
| GB | 1065031 | * | 4/1967 |
| JP | 60-179204 A | | 9/1985 |
| JP | 62-52562 A | | 3/1987 |

(Continued)

OTHER PUBLICATIONS

English abstract of JP 05269919 A, Oct. 19, 1993, 7 pages, Japan.*
English abstract of JP 2001029452 A, Feb. 6, 2001, 3 pages, Japan.*
International Search Report and Written Opinion of the International Searching Authority (Forms PCT/ISA/237 and PCT/ISA/210), dated Dec. 22, 2014, for International Application No. PCT/JP2014/076893, with an English translation of the Search Report.

*Primary Examiner* — Tae H Yoon

(74) *Attorney, Agent, or Firm* — Birch, Stewart, Kolasch & Birch LLP

(57) ABSTRACT

Provided are surface-modified metals such as metal medical devices e.g., guide wires, syringe needles, and metal tubes in medical devices or equipment, and methods for modifying a metal surface, wherein a lubricant layer is firmly bonded to the surface to impart lubricity to the surface and, further, improve the durability of the lubricant layer on the surface, thereby suppressing deterioration of the sliding properties. Included is a surface-modified metal having a surface at least partially treated by polymerization of a monomer in the presence of a thermal polymerization initiator.

9 Claims, No Drawings

(56) References Cited

FOREIGN PATENT DOCUMENTS

| | | |
|---|---|---|
| JP | 2-40322 A | 2/1990 |
| JP | 4-357951 A | 12/1992 |
| JP | 4-362104 A | 12/1992 |
| JP | 05269919 * | 10/1993 |
| JP | 6-510322 A | 11/1994 |
| JP | 8-325524 A | 12/1996 |
| JP | 2001-29452 A | 2/2001 |
| JP | 2005-528253 A | 9/2005 |
| JP | 2011-513566 A | 4/2011 |
| WO | WO 03/097117 A1 | 11/2003 |
| WO | WO 2005/081840 A2 | 8/2005 |
| WO | WO 2006/056482 A1 | 6/2006 |
| WO | WO 2012/032283 A1 | 3/2012 |

* cited by examiner

SURFACE-MODIFIED METAL AND METHOD FOR MODIFYING METAL SURFACE

TECHNICAL FIELD

The present invention relates to surface-modified metals and methods for modifying a metal surface.

BACKGROUND ART

Guide wires and the like used for assisting insertion of a medical device, such as a catheter, into the body are inserted into and optionally placed in blood vessels, respiratory tracts, urethra, or other body cavities or tissues. When a medical device such as a catheter or guide wire is inserted into the body, the medical device may damage the tissue or the like in the body and produce inflammation or cause pain to the patient. To ameliorate these problems, it has been desired to improve the sliding properties of the medical devices intended to be inserted into the body.

To ameliorate the above problems, a method has been proposed in which the surface of a medical device such as a catheter or guide wire is coated with a hydrophilic resin, a fluororesin or the like.

Moreover, the insertion of a syringe needle into the body may also damage the tissue or the like in the body and cause pain to the patient.

Furthermore, if the inner surface of a syringe needle, a metal tube in a medical device or equipment, or the like has reduced lubricity when in a wet condition, there may be difficulties in rapidly and accurately delivering chemicals or blood. Thus, it has been desired to improve and maintain the lubricity of the inner surface of these products in a wet condition.

SUMMARY OF INVENTION

Technical Problem

As described above, there have been needs to improve the sliding properties of medical devices and syringe needles, and to improve and maintain the lubricity of the inner surface of syringe needles, metal tubes in medical devices or equipment, and the like in a wet condition. Various methods have therefore been tried to impart lubricity to the surface of medical devices such as catheters and guide wires to improve the sliding properties thereof.

However, all the methods only allow the surface of medical devices to be coated with a resin or to be cured after the coating. Especially in the case where the surface of the medical device is made of a metal, since the coating resin is not firmly bonded to the surface of the medical device, it can be easily peeled or removed from the surface of the medical device, with the result that unfortunately the sliding properties of the medical device are deteriorated. Accordingly, the development of metal medical devices in which deterioration of sliding properties is suppressed has been desired. In addition, there is still room for improvement in improving and maintaining the lubricity of the inner surface of syringe needles, metal tubes in medical devices or equipment, and the like in a wet condition.

The present invention aims to solve the above problems and provide surface-modified metals such as metal medical devices, e.g., guide wires, syringe needles, and metal tubes in medical devices or equipment, and methods for modifying a metal surface, wherein a lubricant layer is firmly bonded to the surface to impart lubricity to the surface and, further, improve the durability of the lubricant layer on the surface, thereby suppressing deterioration of the sliding properties.

Solution to Problem

The present invention encompasses a surface-modified metal, having a surface at least partially treated by polymerization of a monomer in the presence of a thermal polymerization initiator.

The thermal polymerization initiator is preferably present as an adsorbate on the surface.

The surface is preferably treated with a silane coupling agent prior to the polymerization of a monomer in the presence of a thermal polymerization initiator.

The surface is preferably further treated, after the polymerization of a monomer in the presence of a thermal polymerization initiator, by polymerization of a monomer at least once in the presence of a thermal polymerization initiator optionally present as an adsorbate on the surface.

The monomer is preferably at least one selected from the group consisting of a hydrophilic monomer, a metal salt-containing hydrophilic monomer, and a halogen-containing hydrophilic monomer.

The silane coupling agent is preferably a vinyl group-containing compound.

The surface-modified metal preferably includes stainless steel or a nickel-titanium alloy.

The present invention also encompasses a medical device, including the surface-modified metal.

The medical device is preferably a guide wire, a syringe needle, or a tube of a medical instrument.

The present invention further encompasses a method for modifying a metal surface, including the step of growing polymer chains on the metal surface by polymerizing a monomer in the presence of a thermal polymerization initiator on the metal surface.

The method preferably includes the step of treating the metal surface with a silane coupling agent prior to the step of growing polymer chains.

The method preferably includes, after the step of growing polymer chains, the step of further polymerizing a monomer at least once in the presence of a thermal polymerization initiator optionally present as an adsorbate on the surface.

Advantageous Effects of Invention

According to the present invention, since a metal surface is treated by polymerization of a monomer in the presence of a thermal polymerization initiator, a polymer derived from the monomer is consequently chemically bonded to the metal surface to impart lubricity to the metal surface and, further, improve the durability of the lubricant layer on the surface, thereby suppressing deterioration of the sliding properties of the metal.

DESCRIPTION OF EMBODIMENTS

The surface-modified metals of the present invention have a surface at least partially treated by polymerization of a monomer in the presence of a thermal polymerization initiator.

Lubricant layers formed on metal surfaces by conventional surface treatment or coating methods are not chemically bonded to the surfaces and can be easily peeled or removed by a stress such as rubbing by a hand, friction with an object contacting the metal (e.g., a catheter or cells in the body when the metal is a guide wire), flows of chemicals or blood, or the like. Thus, they are disadvantageous in terms of maintaining durability and sliding properties. In contrast, in the case of the surface-modified metals of the present invention, the surface treatment in which a monomer is polymerized in the presence of a thermal polymerization initiator allows a polymer derived from the monomer to be chemically bonded to the metal surface. This inhibits peeling or removal of the lubricant layer on the metal surface due to a stress, friction, liquid flows, or the like, so that deterioration of the sliding properties of the metal can be suppressed.

The surface-modified metals of the present invention have a surface treated by polymerization of a monomer in the presence of a thermal polymerization initiator, at least at a portion where lubricity is required. The entire surface of the surface-modified metal may be treated as above.

Examples of the thermal polymerization initiator include azo compounds and peroxide compounds. Preferred among these are azo compounds. These thermal polymerization initiators may be used alone or in combinations of two or more.

Examples of azo compounds that can be used as the thermal polymerization initiator include azobisisobutyronitrile (AIBN), 2,2'-azobis[2-(2-imidazolin-2-yl)propane]dihydrochloride, 2,2'-azobis[2-(2-imidazolin-2-yl)propane] disulfate dihydrate, 2,2'-azobis(2-methylpropionamidine) dihydrochloride, 2,2'-azobis[N-(2-carboxyethyl)-2-methylpropionamidine]hydrate, 2,2'-azobis[2-(2-imidazolin-2-yl)propane], 2,2'-azobis(1-imino-1-pyrrolidino-2-methylpropane) dihydrochloride, 2,2'-azobis[2-methyl-N-(2-hydroxyethyl)propionamide], 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 1,1'-azobis(cyclohexane-1-carbonitrile), 2,2'-azobis[N-(2-propenyl)-2-methylpropionamide], 1,1'-azobis(1-acetoxy-1-phenylethane), dimethyl 2,2'-azobisisobutyrate, and derivatives of these compounds. Among these, suitable are azobisisobutyronitrile and derivatives thereof.

Examples of peroxide compounds that can be used as the thermal polymerization initiator include PERHEXA (registered trademark) V (n-butyl 4,4-di(t-butylperoxy)valerate), PERHEXA (registered trademark) C (1,1-di(t-butylperoxy) cyclohexane), PERCUMYL (registered trademark) H (cumene hydroperoxide), PERCUMYL (registered trademark) P (diisopropylbenzene hydroperoxide), PERBUTYL (registered trademark) C (t-butyl cumyl peroxide), PERHEXYL (registered trademark) D (di-t-hexyl peroxide), PEROYL (registered trademark) L (dilauroyl peroxide), PEROYL (registered trademark) NPP (di-n-propyl peroxydicarbonate), PEROYL (registered trademark) SBP (di-sec-butyl peroxydicarbonate), PERCUMYL (registered trademark) ND (cumyl peroxyneodecanoate), PERHEXA (registered trademark) 25O (2,5-dimethyl-2,5-di(2-ethylhexanoylperoxy)hexane), PERBUTYL (registered trademark) O (t-butyl peroxy-2-ethylhexanoate), PERBUTYL (registered trademark) L (t-butyl peroxylaurate), PERBUTYL (registered trademark) I (t-butyl peroxy isopropyl monocarbonate), PERHEXYL (registered trademark) Z (t-hexyl peroxybenzoate), PERHEXA (registered trademark) 25Z (2,5-dimethyl-2,5-di(benzoylperoxy)hexane), and PERBUTYL (registered trademark) Z (t-butyl peroxybenzoate), all available from NOF Corporation.

In the polymerization of a monomer in the presence of the thermal polymerization initiator, the existence form of the thermal polymerization initiator is not particularly limited as long as the monomer is polymerized in conditions where the thermal polymerization initiator coexists with the monomer. Preferably, the thermal polymerization initiator is present as an adsorbate on the surface of a metal.

In an exemplary method for adsorbing the thermal polymerization initiator, e.g., an azo compound or a peroxide compound, to the surface of a metal, the surface portion of the metal to be modified is treated with a solution of the azo compound or peroxide compound dissolved in an organic solvent. This treatment allows the azo compound or peroxide compound to be adsorbed on the metal surface, so that thermal polymerization initiation points are formed, optionally after evaporating the organic solvent by drying. The surface may be treated by any method that allows the solution of the azo compound or peroxide compound to be brought into contact with the metal surface. Suitable methods include, for example, application or spraying of the azo or peroxide compound solution, and immersion into the solution. Moreover, if only part of the surface needs to be modified, it is sufficient to adsorb the thermal polymerization initiator only to the necessary part of the surface. In this case, for example, application or spraying of the solution is suitable.

Examples of the organic solvent include methanol, ethanol, acetone, benzene, toluene, methyl ethyl ketone, ethyl acetate, and tetrahydrofuran (THF). Preferred are aqueous organic solvents such as methanol, ethanol, and acetone because they are quickly dried or evaporated. More preferred are methanol, ethanol and acetone.

In an exemplary polymerization of a monomer in the presence of a thermal polymerization initiator, the thermal polymerization initiator adsorbed to a metal surface generates a radical by heat, and then the radical is transferred to the metal surface and, starting from this radical, a monomer is thermally polymerized. In particular, the monomer is preferably subjected to thermal radical polymerization by heating to 40° C. to 90° C. to grow polymer chains on the metal surface.

In an exemplary method for the polymerization of a monomer, a (liquid) monomer or a solution thereof is applied or coated (sprayed) onto a metal surface where a thermal polymerization initiator such as an azo compound or peroxide compound is present or adsorbed, or the metal is immersed in a (liquid) monomer or a solution thereof, followed by heating. This allows the radical polymerization (thermal radical polymerization) of the monomer to proceed so that polymer chains are grown on the metal surface. In another exemplary method, after the application, coating, spraying, or immersion, the metal surface may be covered with a transparent cover of glass, PET, polycarbonate, or the like and heated therethrough.

In addition to the above methods, the following exemplary method for the polymerization of a monomer may be used: a thermal polymerization initiator such as an azo compound or peroxide compound and a monomer are mixed with water or an organic solvent capable of dissolving the thermal polymerization initiator and a later-described solvent capable of dissolving the monomer to prepare a mixed solution, which is then applied or coated (sprayed) onto a metal surface, or the metal is immersed in the mixed solution, followed by heating.

The solvent for application (spraying), the method for application (spraying), the method for immersion, the conditions for heating, and the like may be conventionally known materials or methods. The solution of the monomer used is an aqueous solution of the monomer or a solution of the monomer dissolved in an organic solvent that hardly dissolves or does not dissolve the thermal polymerization initiator used (e.g., an azo compound). The (liquid) monomer or a solution thereof used may contain a known polymerization inhibitor such as 4-methylphenol.

In the present invention, the radical polymerization of the monomer is allowed to proceed by heating after the application of the (liquid) monomer or a solution thereof or after the immersion into the (liquid) monomer or a solution thereof. The time period of the polymerization may be appropriately chosen. Moreover, in order to prevent inhibition of the polymerization due to active gas such as oxygen in the reaction vessel, it is preferable to remove oxygen from the reaction vessel and the reaction solution during or before heating. Thus, for example, a method may appropriately be employed in which an inert gas such as nitrogen gas or argon gas is inserted into the reaction vessel and the reaction solution to discharge active gas such as oxygen from the reaction system and thereby replace the atmosphere in the reaction system with the inert gas. Oxygen may also be removed by vacuum deaeration.

The heating temperature for the polymerization of a monomer is preferably 40° C. to 90° C., more preferably 50° C. to 80° C. Heating at the above-mentioned temperature allows polymer chains to be formed well on the metal surface. In contrast, heating at lower than 40° C. may be insufficient to polymerize the monomer, while heating at higher than 90° C. may not allow for the use of the aqueous organic solvent and such heating in other organic solvents may increase the burden on the environment.

The heating time for the polymerization of a monomer is not particularly limited and may be appropriately chosen to allow the polymerization of a monomer to proceed sufficiently. In particular, the heating time is preferably 10 to 6000 minutes. The heating time within the above range allows polymer chains to be formed well on the metal surface. More preferably, the heating time is 30 minutes or longer, still more preferably 60 minutes or longer, while it is more preferably 3000 minutes or shorter, still more preferably 2500 minutes or shorter, particularly preferably 600 minutes or shorter.

The monomer to be polymerized in the presence of the thermal polymerization initiator is preferably at least one selected from the group consisting of a hydrophilic monomer, a metal salt-containing hydrophilic monomer, and a halogen-containing hydrophilic monomer. Examples of the hydrophilic monomer include hydrophilic monomers such as acrylic acid, acrylamide, and acrylonitrile, and ionic monomers having an ionic group in a substituent, a side chain or the like. Examples of the ionic monomer include monomers (cationic monomers) having a positive charge such as ammonium and phosphonium; and monomers (anionic monomers) having a negative charge, such as a sulfonic acid group, a carboxyl group, a phosphoric acid group, and a phosphonic acid group, or containing an acidic group that can be dissociated into a negatively charged group.

Specific examples of the ionic monomer include acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, styrenesulfonic acid, and amine salts thereof; allylamine, 2-dimethylaminoethyl (meth)acrylate, and their hydrohalic acid salts; and 3-trimethylammonium propyl (meth)acrylate, 3-trimethylammonium propyl (meth)acrylamide, N,N,N-trimethyl-N-(2-hydroxy-3-methacryloyloxypropyl) ammonium chloride, and 2-(methacryloyloxy)ethyltrimethylammonium chloride (methacroylcholine chloride).

The hydrophilic monomer may suitably be a zwitterionic monomer (zwitterionic group-containing compound: compound bearing a center of permanent positive charge and a center of negative charge) such as a carboxybetaine, sulfobetaine, or phosphobetaine. The zwitterionic monomer may be a compound represented by Formula (1) below and preferably suitably a compound represented by Formula (2) below, because then excellent sliding properties and excellent durability can be achieved.

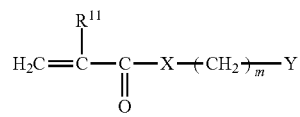

(1)

In Formula (1), $R^{11}$ represents —H or —CH$_3$; X represents —O— or —NH—; m represents an integer of 1 or more; and Y represents a zwitterionic group.

In Formula (1), preferably $R^{11}$ is —CH$_3$, X is —O—, and m is an integer of 1 to 10. In the zwitterionic group designated by Y, the cation may be a quaternary ammonium such as tetraalkylammonium, and the anion may be a carboxylic acid, sulfonic acid, phosphate or the like.

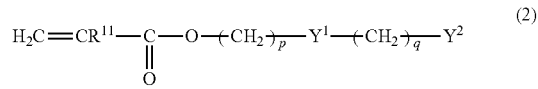

(2)

In Formula (2), $R^{11}$ represents —H or —CH$_3$; p and q each represent an integer of 1 or more; and $Y^1$ and $Y^2$ represent ionic functional groups having charges opposite to each other.

In Formula (2), p is preferably an integer of 2 or more, more preferably an integer of 2 to 10, and q is preferably an integer of 1 to 10, more preferably an integer of 2 to 4. Moreover, $R^{11}$ is preferably as defined above. $Y^1$ and $Y^2$ are as defined for the cation and anion above.

Typical suitable examples of the zwitterionic monomer include compounds represented by Formulae (2-1) to (2-4) below.

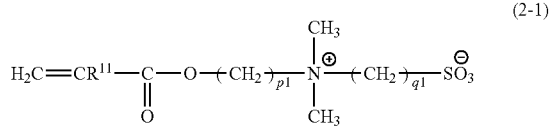

(2-1)

In Formula (2-1), $R^{11}$ represents a hydrogen atom or a methyl group, and p1 and q1 each represent an integer of 1 to 10.

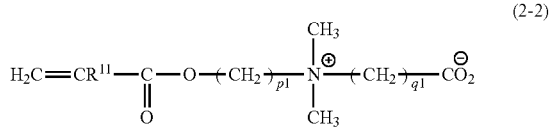

(2-2)

In Formula (2-2), $R^{11}$ represents a hydrogen atom or a methyl group, and p1 and q1 each represent an integer of 1 to 10.

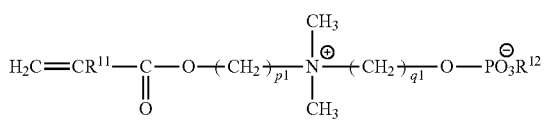

(2-3)

In Formula (2-3), $R^{11}$ represents a hydrogen atom or a methyl group, $R^{12}$ represents a C1-C6 hydrocarbon group, and p1 and q1 each represent an integer of 1 to 10.

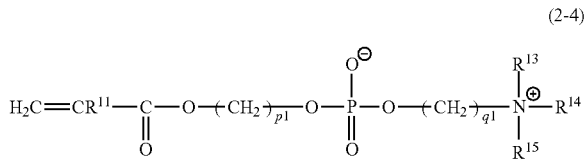

(2-4)

In Formula (2-4), $R^{11}$ represents a hydrogen atom or a methyl group; $R^{13}$, $R^{14}$, and $R^{15}$ are the same as or different from one another and each represent a C1 or C2 hydrocarbon group; and p1 and q1 each represent an integer of 1 to 10.

Examples of the compound represented by Formula (2-1) include dimethyl(3-sulfopropyl)(2-(meth)acryloyloxyethyl)ammonium betaine and [2-(methacryloyloxy)ethyl]dimethyl(3-sulfopropyl)aminium hydroxide. Examples of the compound represented by Formula (2-2) include dimethyl(2-carboxyethyl)-(2-(meth)acryloyloxyethyl)ammonium betaine. Examples of the compound represented by Formula (2-3) include dimethyl(3-methoxyphosphopropyl)-(2-(meth)acryloyloxyethyl)ammonium betaine. Examples of the compound represented by Formula (2-4) include 2-(meth)acryloyloxyethyl phosphorylcholine.

Examples of the metal salt-containing hydrophilic monomer include metal salts of acids such as acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, and styrenesulfonic acid.

The metal salt is preferably an alkali metal salt, such as sodium or potassium, or an alkaline earth metal salt, such as calcium.

When the monomer used is a hydrophilic monomer containing a carboxylic acid such as acrylic acid or methacrylic acid, it may be converted to a metal salt using sodium hydroxide, potassium hydroxide, sodium hydrogen carbonate or the like after the polymerization reaction.

The halogen-containing hydrophilic monomer may be a monomer containing a hydrophilic group containing a halide salt such as chloride or bromide. Preferred are monomers containing a chloride-containing hydrophilic group and monomers containing a bromide-containing hydrophilic group. Preferred among these are compounds represented by Formula (3) below.

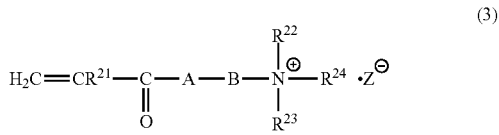

(3)

In Formula (3), A represents an oxygen atom or —NH—; B represents a C1-C4 alkylene group; $R^{21}$ represents a hydrogen atom or a methyl group; $R^{22}$, $R^{23}$, and $R^{24}$ are the same as or different from one another and each represent a C1-C4 alkyl group; and $Z^{\ominus}$ represents a halogen ion.

In Formula (3), A is preferably an oxygen atom. Examples of B include linear or branched alkylene groups such as a methylene group, an ethylene group, or a propylene group, with a methylene group or an ethylene group being preferred. Examples of $R^{22}$, $R^{23}$, and $R^{24}$ include linear or branched alkyl groups such as a methyl group, an ethyl group, or a propyl group, with a methyl group or an ethyl group being preferred. Examples of Z (halogen atom) include fluorine, chlorine, and bromine. Preferred is chlorine or bromine, and particularly preferred is chlorine.

Examples of the nitrogen-containing monomer represented by Formula (3) include 2-(methacryloyloxy)ethyltrimethylammonium chloride, 2-(acryloyloxy)ethyltrimethylammonium chloride, 2-(methacryloyloxy)ethyldimethylethylammonium chloride, and 2-(acryloyloxy)ethyldimethylethylammonium chloride.

In particular, the monomer is particularly preferably at least one selected from the group consisting of acrylic acid, acrylic acid metal salts, methacrylic acid, methacrylic acid metal salts, 3-sulfopropyl methacrylate potassium salt, 2-(methacryloyloxy)ethyltrimethylammonium chloride, 2-methacryloyloxyethyl phosphorylcholine, and [2-(methacryloyloxy)ethyl]dimethyl(3-sulfopropyl)aminium hydroxide as these monomers provide particularly excellent sliding properties and particularly excellent durability.

For excellent sliding properties and excellent durability, polymer chains represented by any of Formulae (4) to (7) below are preferably formed in the polymerization of the monomer. Such formed polymer chains also provide prevention of adsorption or aggregation of proteins.

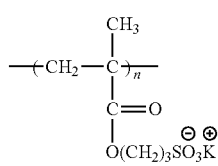

(4)

(n represents an integer of 1 or more.)

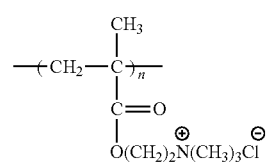

(5)

(n represents an integer of 1 or more.)

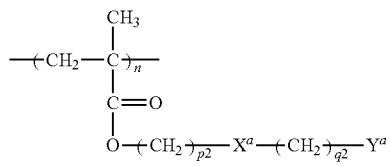

(6)

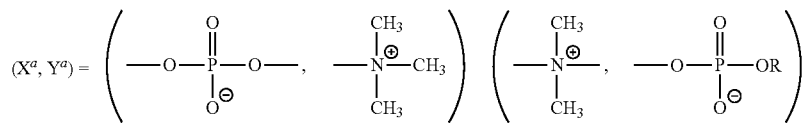

(n represents an integer of 1 or more; p2 ≧ 2; q2 = 2, 3, or 4; represents a hydrocarbon group.)

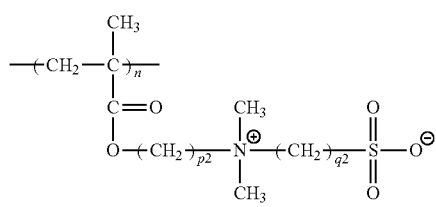

(7)

(n represents an integer of 1 or more; p2 ≧ 2; q2 = 2, 3, or 4)

In Formulae (4) to (7), n (polymerization degree) is preferably 20 to 5000, more preferably 200 to 2000. If n is less than 20, the polymer chains are so short that they may be concealed by irregularities on the metal surface, which tends to result in failure to provide sliding properties. If n is more than 5000, the amount of monomer used is increased, which tends to result in an economic disadvantage. Moreover, examples of the hydrocarbon group for R include a methyl group and an ethyl group.

The length of the formed polymer chain is preferably 10 to 5000 nm, more preferably 50 to 1000 nm. If the length is shorter than 10 nm, good sliding properties tend not to be achieved. If the length is longer than 5000 nm, a further improvement in sliding properties cannot be expected while the cost of starting materials tends to increase due to the use of the expensive monomer. In addition, surface patterns generated by the surface treatment tend to be visible to the naked eyes and thereby spoil the appearance.

In the polymerization of a monomer, one kind of monomer or two or more kinds of monomers may be radically polymerized starting from the polymerization initiation points. Moreover, multiple kinds of polymer chains may be grown on the metal surface.

In the surface-modified metals of the present invention, the polymer chains formed by the polymerization of a monomer may be cross-linked to one another. In this case, the polymer chains may be cross-linked by ionic crosslinking, or crosslinking by a hydrophilic group containing an oxygen atom. Moreover, in the polymerization of a monomer, a slight amount of a compound having at least two vinyl groups in a molecule may be added to introduce crosslinks between the polymer chains during the polymerization.

The compound having at least two vinyl groups in a molecule may suitably be N,N'-methylenebisacrylamide or the like.

The surface-modified metals of the present invention have a surface at least partially treated by polymerization of a monomer in the presence of a thermal polymerization initiator. Preferably, the surface is treated with a silane coupling agent prior to the polymerization of a monomer in the presence of a thermal polymerization initiator. Thus, another suitable embodiment of the present invention is a surface-modified metal having a surface treated with a silane coupling agent prior to the polymerization of a monomer in the presence of a thermal polymerization initiator. As a result of the treatment with a silane coupling agent prior to the polymerization of a monomer in the presence of a thermal polymerization initiator, the polymer is chemically bonded to the metal via the silane coupling agent, so that a stronger bond is formed and leads to a further enhancement of the sliding properties and durability of the surface-modified metal.

The silane coupling agent is not particularly limited. For example, it is preferably a vinyl group-containing compound that contains a hydrolyzable group and a vinyl group because then a radical can be easily generated. Such a vinyl group-containing compound can react with and bond to a hydroxy group present on the metal surface via the hydrolyzable group, and its vinyl group can form a polymerization initiation point for the monomer. Consequently, polymer chains grown starting from the polymerization initiation points are chemically bonded to the metal via the silane coupling agent. More preferred as the silane coupling agent are vinyltrimethoxysilane, vinyltriethoxysilane, (3-acryloyloxypropyl)trimethoxysilane, (3-acryloyloxypropyl)triethoxysilane, (3-methacryloyloxypropyl)trimethoxysilane, (3-methacryloyloxypropyl)triethoxysilane, vinylchlorodimethylsilane, (3-acryloyloxypropyl)chlorodimethylsilane, and (3-methacryloyloxypropyl)chlorodimethylsilane. Still more preferred are (3-acryloyloxypropyl)trimethoxysilane, (3-acryloyloxypropyl)triethoxysilane, and (3-acryloyloxypropyl)chlorodimethylsilane. In view of reactivity and safety, particularly preferred is (3-acryloyloxypropyl) trimethoxysilane.

The treatment with a silane coupling agent may be carried out by coating methods such as by application, spraying, immersion, or the like. The treatment is preferably carried out by preparing a silane coupling agent (silane compound)

into an aqueous solution, alcohol solution, acetone solution or the like beforehand, and then coating it onto the metal surface, followed either by drying by heat, or by standing in atmospheric moisture conditions, in wet conditions, or the like to cause hydrolysis and dehydration condensation. Another preferred method includes immersing the metal in the silane coupling agent solution followed by drying by heat. Thus, a chemical bond is formed between the hydroxy group on the metal surface and the silane coupling agent (silane compound), so that they are fixed to each other. The drying temperature and time may be appropriately set, for example, to a temperature and time capable of forming a chemical bond. The drying temperature is preferably 40° C. to 150° C.

In the preparation of an aqueous solution, additional treatment may be performed as appropriate such as by adding alcohol to prepare a mixed water/alcohol solution, or by adjusting the pH to weakly acidic with acetic acid or the like. Such treatment may be performed as appropriate because the solubility of the silane coupling agent in water varies depending on the kind of silane coupling agent.

When the treatment with a silane coupling agent is carried out before the polymerization of a monomer in the presence of a thermal polymerization initiator, the above-described polymerization of a monomer in the presence of a thermal polymerization initiator is carried out after the treatment with a silane coupling agent. In other words, a radical is generated from the hydrocarbon group of the silane coupling agent, such as vinyl, acrylate, or methacrylate group, by means of the thermal polymerization initiator and, starting from this radical, surface-initiated radical polymerization is performed to polymerize the monomer. Thus, a polymer formed from the monomer is chemically bonded to the metal surface via the silane coupling agent, which suppresses deterioration of sliding properties due to friction, rubbing, or flows.

Moreover, a preferred surface-modified metal of the present invention is obtained by the polymerization of a monomer in the presence of a thermal polymerization initiator, followed by further treatment by polymerization of a monomer at least once in the presence of a thermal polymerization initiator optionally present as an adsorbate on the surface.

When the polymerization of a monomer in the presence of a thermal polymerization initiator is followed by further treatment by polymerization of a monomer at least once in the presence of a thermal polymerization initiator optionally present as an adsorbate on the surface, after the above-described polymerization of a monomer in the presence of a thermal polymerization initiator, polymerization of a monomer is performed again at least once in the presence of a thermal polymerization initiator optionally present as an adsorbate on the surface. This means that the treatment by polymerization of a monomer in the presence of a thermal polymerization initiator is performed at least twice. As a result of such treatment, polymer layers are stacked on the metal surface, so that the sliding properties of the resulting surface-modified metal can be further enhanced.

The method for polymerizing a monomer in the second and subsequent treatments is the same as that in the first treatment described above. When the treatment by polymerization of a monomer in the presence of a thermal polymerization initiator is performed at least twice as mentioned above, it is preferable to perform, before the polymerization of a monomer in the (k+1)th treatment, treatment with a thermal polymerization initiator, and then polymerize a monomer in the (k+1)th treatment. After the polymerization of a monomer in the k-th treatment, polymerization of a monomer may be directly subsequently performed in the (k+1)th treatment. Or, after the polymerization of a monomer in the k-th treatment, unreacted monomers and the like may once be washed away from the surface of the resulting surface-modified metal by washing with water, drying and the like, followed by polymerization of a monomer in the (k+1)th treatment. Here, the existence form of the thermal polymerization initiator used in the polymerization of a monomer in the (k+1) th treatment, the method for the treatment with the thermal polymerization initiator prior to the polymerization of a monomer in the (k+1)th treatment, and the kind of thermal polymerization initiator used are as described above.

It is to be noted that "k" in the present paragraph represents an integer of 1 or more.

Moreover, in the treatment method, the monomer used in the first treatment and the monomers used in the second or subsequent treatment may be the same as or different from each other. Furthermore, when the number of second and subsequent treatments is more than one, the monomers used in the plurality of treatments may be the same as or different from each other.

Particularly from the economical standpoint, when the treatment by polymerization of a monomer is performed n times (where n is an integer of 2 or more), it is more preferable to use in the first to (n−1)th treatments relatively inexpensive monomers such as acrylic acid, acrylamide, or acrylonitrile, and in the n-th treatment the aforementioned zwitterionic monomer such as 2-(meth)acryloyloxyethyl phosphorylcholine, or [2-(methacryloyloxy)ethyl]dimethyl (3-sulfopropyl)aminium hydroxide, the aforementioned metal salt-containing hydrophilic monomer such as a metal salt of an acid such as 3-sulfopropyl (meth)acrylate, or the aforementioned halogen-containing hydrophilic monomer such as 2-(methacryloyloxy)ethyltrimethylammonium chloride (methacroylcholine chloride) because then sliding properties are further improved even as compared to when, for example, the metal salt-containing hydrophilic monomer is used for n times.

Thus, in another suitable embodiment of the present invention, the surface-modified metal is obtained by polymerization of at least one monomer selected from the group consisting of acrylic acid, acrylamide, and acrylonitrile in the presence of the thermal polymerization initiator, followed by further treatment by polymerization of at least one monomer selected from the group consisting of 2-(meth) acryloyloxyethyl phosphorylcholine, 3-sulfopropyl (meth) acrylate potassium salt, [2-(methacryloyloxy)ethyl]dimethyl (3-sulfopropyl)-aminium hydroxide, and methacroylcholine chloride at least once in the presence of a thermal polymerization initiator optionally present as an adsorbate on the surface.

As described above, the surface-modified metals of the present invention are obtained by forming polymerization initiation points on the surface of a metal using a thermal polymerization initiator, and polymerizing a monomer starting from the polymerization initiation points to grow polymer chains on the metal surface.

Thus, the present invention also encompasses methods for modifying a metal surface, including the step of growing polymer chains on the metal surface by polymerizing a monomer in the presence of a thermal polymerization initiator on the metal surface.

In the above step, first, polymerization initiation points are formed on the surface of a metal. This can be accomplished, for example, by adsorbing the thermal polymerization initiator on the metal surface to form polymerization initiation points.

The thermal polymerization initiator is as described above. The method for adsorbing the thermal polymerization initiator on the metal surface and the method for heating are also as described above.

In the above step, a monomer is polymerized (radically polymerized) starting from the polymerization initiation points to grow polymer chains on the metal surface. The kind of monomer and the polymerization method are as described above.

The methods for modifying a metal surface may further include, before the above step, the step of reacting the metal with a silane coupling agent to bond the silane coupling agent to the metal surface. Thus, in another suitable embodiment of the present invention, the method for modifying a metal surface includes the step of treating the metal surface with a silane coupling agent prior to the step of growing polymer chains.

The kind of silane coupling agent and the method for reacting the metal and the silane coupling agent are as described above.

Moreover, the methods for modifying a metal surface may include, after the step of growing polymer chains, the step of further polymerizing a monomer at least once in the presence of a thermal polymerization initiator optionally present as an adsorbate on the surface. Repeating at least twice the step of polymerizing a monomer in the presence of a thermal polymerization initiator as described above allows the surface-modified metal to have more improved sliding properties. The method for repeating at least twice the treatment of polymerizing a monomer in the presence of a thermal polymerization initiator, the kind of monomer used, the existence form of the thermal polymerization initiator, the method for treatment with the thermal polymerization initiator, the kind of thermal polymerization initiator used, and the like are as described above.

Exemplary materials of the surface-modified metals of the present invention include metals such as stainless steel, nickel-titanium alloys, iron, titanium, aluminum, tin, and zinc-tungsten alloys. Among these, stainless steel and nickel-titanium alloys are preferred in view of bonding between the metal surface and the lubricant layer and biocompatibility. Thus, in another suitable embodiment of the present invention, the surface-modified metal of the present invention includes stainless steel or a nickel-titanium alloy.

In the surface-modified metals of the present invention, the metal surface is imparted with lubricity and, further, the durability of the lubricant layer on the surface is improved so that deterioration of the sliding properties of the metal can be suppressed. Such metals can be suitably used for example for metal medical devices, e.g., guide wires, syringe needles, metal tubes in medical devices or equipment, and other medical devices. Thus, the present invention also encompasses medical devices including the surface-modified metal. In another suitable embodiment of the present invention, the medical device is a guide wire, a syringe needle, or a tube of a medical instrument.

Moreover, by applying the modification method to at least part of a three-dimensional metal, a surface-modified three-dimensional metal can be obtained. Further, preferred examples of such a modified metal surface include polymer brushes. The polymer brush as used herein refers to an assembly of graft polymer molecules obtained in the "grafting from" approach by surface-initiated living radical polymerization. Moreover, the graft chains are preferably oriented in a direction substantially vertical to the metal surface because then entropy is reduced and thus the molecular mobility of the graft chains is reduced to provide sliding properties. Furthermore, semidilute or concentrated brushes which have a brush density of 0.01 chains/nm$^2$ or higher are preferred.

EXAMPLES

The present invention is more specifically described by reference to examples below but is not limited only to these examples.

Example 1

The surface of a SUS flat plate (10 cm square, 1 mm in thickness) was washed with acetone and then dried.

The plate was immersed in a 2% by mass aqueous solution of (3-acryloyloxypropyl)trimethoxysilane (with 2% by mass of acetic acid) for 10 minutes, and then taken out from the solution and dried at 40° C. for 24 hours. Then, the plate was washed with water and subsequently with acetone. The thus treated SUS plate was immersed in a 1.5% by mass solution of azobisisobutyronitrile (AIBN) in ethanol for 5 minutes, and then taken out and dried.

The resulting SUS plate was placed in a glass vessel containing a 1.25 M aqueous solution of 3-sulfopropyl methacrylate potassium salt, and the glass vessel was covered with a lid.

After the glass vessel was purged with argon, it was heated in a 60° C. water bath for 5 hours to cause surface-initiated radical polymerization. Thereafter, the surface was washed with water to wash away unreacted monomers and the like. In this manner, a surface-modified metal was obtained. The surface-modified metal was evaluated for sliding properties as described later.

Example 2

A surface-modified metal was obtained by carrying out surface-initiated radical polymerization in the same manner as in Example 1, except that the SUS plate was changed to a SUS guide wire (core wire). The surface-modified metal was evaluated for sliding properties as described later.

Example 3

A surface-modified metal was obtained by carrying out surface-initiated radical polymerization in the same manner as in Example 2, except that the SUS guide wire (core wire) was changed to a nickel-titanium alloy guide wire. The surface-modified metal was evaluated for sliding properties as described later.

Example 4

A surface-modified metal was obtained by carrying out surface-initiated radical polymerization in the same manner as in Example 1 without the treatment with (3-acryloyloxypropyl)trimethoxysilane. The surface-modified metal was evaluated for sliding properties as described later.

Example 5

A surface-modified metal was obtained by carrying out surface-initiated radical polymerization in the same manner as in Example 1, except that 3-sulfopropyl methacrylate potassium salt was changed to 2-(methacryloyloxy)ethyltrimethylammonium chloride. The surface-modified metal was evaluated for sliding properties as described later.

Example 6

A surface-modified metal was obtained by carrying out surface-initiated radical polymerization in the same manner as in Example 1, except that 3-sulfopropyl methacrylate potassium salt was changed to 2-methacryloyloxyethyl phosphorylcholine. The surface-modified metal was evaluated for sliding properties as described later.

Example 7

A surface-modified metal was obtained by carrying out surface-initiated radical polymerization in the same manner as in Example 1, except that 3-sulfopropyl methacrylate potassium salt was changed to [2-(methacryloyloxy)ethyl] dimethyl-(3-sulfopropyl) aminium hydroxide. The surface-modified metal was evaluated for sliding properties as described later.

Example 8

The surface of a SUS flat plate (10 cm square, 1 mm in thickness) was washed with acetone and then dried.
The washed SUS plate was placed in a glass vessel containing 0.02 M azobisisobutyronitrile (AIBN) and 1.2 M 3-sulfopropyl methacrylate potassium salt in a water/ethanol (1:1) mixed solution, and the glass vessel was covered with a lid.
After the glass vessel was purged with argon, it was heated in a 60° C. water bath for 5 hours to cause surface-initiated radical polymerization. Thereafter, the surface was washed with water to wash away unreacted monomers and the like. In this manner, a surface-modified metal was obtained. The surface-modified metal was evaluated for sliding properties as described later.

Example 9

A surface-modified metal was obtained by carrying out surface-initiated radical polymerization in the same manner as in Example 8, except that 3-sulfopropyl methacrylate potassium salt was changed to 2-(methacryloyloxy)ethyltrimethylammonium chloride. The surface-modified metal was evaluated for sliding properties as described later.

Example 10

The surface of a SUS flat plate (10 cm square, 1 mm in thickness) was washed with acetone and then dried.
The washed SUS plate was immersed in a 1.5% by mass solution of azobisisobutyronitrile (AIBN) in ethanol for 5 minutes, and then taken out and dried. Then, the plate was placed in a glass vessel containing a 1.2 M aqueous solution of acrylic acid, and the glass vessel was covered with a lid.
After the glass vessel was purged with argon, it was heated in a 60° C. water bath for 3 hours to cause surface-initiated radical polymerization. Thereafter, the surface was washed with water to wash away unreacted monomers and the like.
Next, the washed SUS plate was again immersed in a 1.5% by mass solution of azobisisobutyronitrile (AIBN) in ethanol for 5 minutes, and then taken out and dried. Then, the plate was placed in a glass vessel containing an aqueous solution of 1.2 M 3-sulfopropyl methacrylate potassium salt, and the glass vessel was covered with a lid.
After the glass vessel was purged with argon, it was heated in a 60° C. water bath for 5 hours to cause surface-initiated radical polymerization. Thereafter, the surface was washed with water to wash away unreacted monomers and the like. In this manner, a surface-modified metal was obtained. The surface-modified metal was evaluated for sliding properties as described later.

Example 11

A surface-modified metal was obtained by carrying out surface-initiated radical polymerization in the same manner as in Example 10, except that 3-sulfopropyl methacrylate potassium salt was changed to 2-(methacryloyloxy)ethyltrimethylammonium chloride. The surface-modified metal was evaluated for sliding properties as described later.

Example 12

The surface of a SUS flat plate (10 cm square, 1 mm in thickness) was washed with acetone and then dried.
The washed SUS plate was placed in a glass vessel containing 0.02 M azobisisobutyronitrile (AIBN) and 1.2 M acrylic acid in a water/ethanol (1:1) mixed solution, and the glass vessel was covered with a lid.
After the glass vessel was purged with argon, it was heated in a 60° C. water bath for 3 hours to cause surface-initiated radical polymerization. Thereafter, the surface was washed with water to wash away unreacted monomers and the like.
Next, the washed SUS plate was placed in a glass vessel containing 0.02 M azobisisobutyronitrile (AIBN) and 1.2 M 3-sulfopropyl methacrylate potassium salt in a water/ethanol (1:1) mixed solution, and the glass vessel was covered with a lid.
After the glass vessel was purged with argon, it was heated in a 60° C. water bath for 5 hours to cause surface-initiated radical polymerization. Thereafter, the surface was washed with water to wash away unreacted monomers and the like. In this manner, a surface-modified metal was obtained. The surface-modified metal was evaluated for sliding properties as described later.

Comparative Example 1

The surface of a SUS flat plate (10 cm square, 1 mm in thickness) washed with acetone and then dried was evaluated for sliding properties as described later.

Comparative Example 2

A SUS guide wire (core wire) only washed with acetone and then dried was evaluated for sliding properties as described later.

Comparative Example 3

The surface of a SUS flat plate (10 cm square, 1 mm in thickness) was washed with acetone and then dried. A maleic anhydride-based polymer, which is a common lubricant, was applied to the surface of the dried plate to prepare a comparative surface-modified metal. The comparative surface-modified metal was evaluated for sliding properties as described later.

<Evaluation of Sliding Properties>

Each surface-modified metal, comparative surface-modified metal, flat plate, or guide wire was watered and rubbed by a hand to evaluate sliding properties.

As a result of the evaluation, the surfaces of Comparative Examples 1 and 2 were found not to be slippery but to have a feel like their original SUS surface and thus have low sliding properties. When compared to these surfaces, the surfaces of Comparative Example 3 and Examples 1 to 12 were slippery and had significantly improved sliding properties. Particularly, the surfaces of Examples 10 to 12 were more slippery and had more improved sliding properties than the surface of Example 1.

Moreover, the surfaces of Examples 1 to 12 remained slippery and showed no change in sliding properties after rubbing 500 times by a hand. The surface of Comparative Example 3 had similar sliding properties to the initial sliding properties until it was rubbed 150 times by a hand. Thereafter, however, the sliding properties of Comparative Example 3 gradually deteriorated, reaching similar sliding properties to that of Comparative Example 1 after rubbing 500 times.

The invention claimed is:

1. A method for producing a surface-modified metal, said method comprising:
   a step of treating the metal surface with a silane coupling agent, and
   a step of growing polymer chains from the silane coupling agent located on the treated metal surface by polymerizing a monomer in the presence of a thermal polymerization initiator via surface-initiated radical polymerization on the treated metal surface, thereby obtaining the surface-modified metal,
   wherein the thermal polymerization initiator is an azo compound,
   wherein the monomer is at least one selected from the group consisting of a hydrophilic monomer, a metal salt-containing hydrophilic monomer, and a halogen-containing hydrophilic monomer,
   wherein the silane coupling agent is vinyltrimethoxysilane, vinyltriethoxysilane, (3-acryloyloxypropyl)trimethoxysilane, (3-acryloyloxypropyl)triethoxysilane, (3-methacryloyloxypropyl)trimethoxysilane, (3-methacryloyloxypropyl)triethoxysilane, vinylchlorodimethylsilane, (3-acryloyloxypropyl)chlorodimethylsilane, or (3-methacryloyloxypropyl)chlorodimethylsilane.

2. The method for producing a surface-modified metal according to claim 1, wherein the thermal polymerization initiator is present as an adsorbate on the surface.

3. The method for producing a surface-modified metal according to claim 1, further comprising, after the step of growing polymer chains, a step of further polymerizing a monomer at least once in the presence of a thermal polymerization initiator.

4. The method for producing a surface-modified metal according to claim 1, wherein the metal comprises stainless steel or a nickel-titanium alloy.

5. A method for producing a medical device, comprising the method for producing a surface-modified metal according to claim 1, wherein the metal surface is part of a medical device.

6. The method for producing a medical device according to claim 5, wherein the medical device is a guide wire, a syringe needle, or a tube of a medical instrument.

7. A method for modifying a metal surface, comprising:
   a step of treating the metal surface with a silane coupling agent, and
   a step of growing polymer chains from the silane coupling agent located on the treated metal surface by polymerizing a monomer in the presence of a thermal polymerization initiator via surface-initiated radical polymerization on the treated metal surface,
   wherein the thermal polymerization initiator is an azo compound,
   wherein the monomer is at least one selected from the group consisting of a hydrophilic monomer, a metal salt-containing hydrophilic monomer, and a halogen-containing hydrophilic monomer,
   wherein the silane coupling agent is vinyltrimethoxysilane, vinyltriethoxysilane, (3-acryloyloxypropyl)trimethoxysilane, (3-acryloyloxypropyl)triethoxysilane, (3-methacryloyloxypropyl)trimethoxysilane, (3-methacryloyloxypropyl)triethoxysilane, vinylchlorodimethylsilane, (3-acryloyloxypropyl)chlorodimethylsilane, or (3-methacryloyloxypropyl)chlorodimethylsilane.

8. The method for modifying a metal surface according to claim 7, further comprising, after the step of growing polymer chains, a step of further polymerizing a monomer at least once in the presence of a thermal polymerization initiator.

9. A method for producing a surface-modified metal, said method comprising:
   a step of growing polymer chains from a silane coupling agent located on a metal surface by polymerizing a monomer in the presence of a first thermal polymerization initiator via surface-initiated radical polymerization on the metal surface containing the silane coupling agent, thereby obtaining the surface-modified metal, and
   after the step of growing polymer chains, a step of further polymerizing a monomer at least once in the presence of a second thermal polymerization initiator,
   wherein the first thermal polymerization initiator is an azo compound,
   wherein the silane coupling agent is vinyltrimethoxysilane, vinyltriethoxysilane, (3-acryloyloxypropyl)trimethoxysilane, (3-acryloyloxypropyl)triethoxysilane, (3-methacryloyloxypropyl)trimethoxysilane, (3-methacryloyloxypropyl)triethoxysilane, vinylchlorodimethylsilane, (3-acryloyloxypropyl)chlorodimethylsilane, or (3-methacryloyloxypropyl)chlorodimethylsilane.

* * * * *